(12) United States Patent
Henry et al.

(10) Patent No.: US 8,870,786 B2
(45) Date of Patent: *Oct. 28, 2014

(54) METHOD AND APPARATUS FOR TINNITUS EVALUATION

(71) Applicants: Oregon Health & Science University, Portland, OR (US); The United States of America, dba The Department of Veterans Affairs, Washington, DC (US)

(72) Inventors: James A. Henry, Portland, OR (US); Grayson Silaski, Portland, OR (US); David Gray, Portland, OR (US); Edward V. Porsov, Portland, OR (US); Kimberly Owens, Portland, OR (US)

(73) Assignees: Oregon Health & Science University, Portland, OR (US); The United States of America as represented by the Secretary of The Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/740,382

(22) Filed: Jan. 14, 2013

(65) Prior Publication Data

US 2013/0131542 A1    May 23, 2013

Related U.S. Application Data

(63) Continuation of application No. 12/374,274, filed as application No. PCT/US2007/073663 on Jul. 17, 2007, now Pat. No. 8,353,846.

(60) Provisional application No. 60/807,696, filed on Jul. 18, 2006.

(51) Int. Cl.
*A61B 5/00* (2006.01)
*A61B 5/12* (2006.01)

(52) U.S. Cl.
CPC .................. *A61B 5/128* (2013.01); *A61B 5/121* (2013.01); *A61B 5/0002* (2013.01); *A61B 5/7435* (2013.01)
USPC ........................................................ 600/559

(58) Field of Classification Search
CPC ...... A61B 5/128; A61B 5/121; A61B 5/0002; A61B 5/7435
USPC ........................... 600/559, 25; 381/73.1, 312
See application file for complete search history.

(56) References Cited

U.S. PATENT DOCUMENTS 4,222,393 A    9/1980   Hocks et al.
4,226,248 A   10/1980   Manoli (Continued)

OTHER PUBLICATIONS

Henry, James A. et al., "Comparison of Two Computer-Automated Procedures for Tinnitus Pitch Matching," Journal of Rehabilitation Research and Development, Sep./Oct. 2001, pp. 557-566, vol. 38, No. 5, U.S. Department of Veterans Affairs, 810 Vermont Avenue, NW, Washington, DC 20420.

(Continued)

*Primary Examiner* — Brian Szmal
(74) *Attorney, Agent, or Firm* — Schwabe, Williamson & Wyatt

(57) ABSTRACT

Methods, articles of manufacture, and systems for evaluating tinnitus are disclosed herein. According to various embodiments, a tinnitus evaluation system may include a tinnitus evaluation module configured to perform one or more tinnitus evaluation tests. A tinnitus evaluation test may comprise generating a first single-frequency sound based at least in part on a sound of a patient's tinnitus, and generating a narrow-band sound centered at the frequency of the first single-frequency sound. Tests include a hearing threshold test, a loudness match test, a pitch match test, a bandwidth match test, a minimum masking level test, and a residual inhibition test.

29 Claims, 10 Drawing Sheets

(56) References Cited

U.S. PATENT DOCUMENTS

| | | | |
|---|---|---|---|
| 4,453,809 | A | 6/1984 | Hill et al. |
| 5,325,872 | A | 7/1994 | Westermann |
| 6,155,971 | A | 12/2000 | Calhoun et al. |
| 6,610,019 | B2 | 8/2003 | Choy |
| 6,631,295 | B2 | 10/2003 | Rubinstein et al. |
| 6,682,472 | B1 | 1/2004 | Davis |
| 6,846,284 | B2 | 1/2005 | Choy |
| 6,974,410 | B2 | 12/2005 | Micheyl et al. |
| 7,081,085 | B2 | 7/2006 | Viirre et al. |
| 8,353,846 | B2 * | 1/2013 | Henry et al. .......... 600/559 |
| 2005/0013445 | A1 | 1/2005 | Martin |
| 2005/0192514 | A1 | 9/2005 | Kearby et al. |
| 2006/0036297 | A1 | 2/2006 | Seidman |
| 2006/0167335 | A1 | 7/2006 | Park et al. |
| 2006/0167376 | A1 | 7/2006 | Viirre et al. |
| 2007/0093733 | A1 | 4/2007 | Choy |

OTHER PUBLICATIONS

Henry, James A. et al., "Computer-Automated Clinical Technique for Tinnitus Quantification," American Journal of Audiology, 2000, 1059-0889, vol. 9, American Speech-Language-Hearing Association, 2200 Research Boulevard, Rockville, MD 20850-3289.

Henry, James A. et al., "Reliability of Tinnitus Loudness Matches under Procedural Variation," Journal of the American Academy of Audiology, Oct. 1999, pp. 502-520, vol. 10, No. 9, 11730 Plaza America Drive, Suite 300, Reston, VA 20190.

Henry, James A., et al., "Reliability of Computer-Automated Hearing Thresholds in Cochlear-Impaired Listeners Using ER-4B Canal Phone TM Earphones," Journal of Rehabilitation Research and Development, May/Jun. 2003, pp. 253-264, vol. 40, No. 3, U.S. Department of Veterans Affairs, 810 Vermont Avenue, NW, Washington, DC 20420.

Henry, James A., et al., "Reliability of Hearing Thresholds: Computer-Automated Testing with ER-4B Canal Phone TM Earphones," Journal of Rehabilitation Research and Development, Sep./Oct. 2001, pp. 567-581, vol. 38, No. 5, U.S. Department of Veterans Affairs, 810 Vermont Avenue, NW, Washington, DC 20420.

Henry, James A., et al., "Comparison of Manual and Computer-Automated Procedures for Tinnitus Pitch-Matching," Journal of Rehabilitation Research and Development, Mar./Apr. 2004, pp. 121-138, vol. 41, No. 2, U.S. Department of Veterans Affairs, 810 Vermont Avenue, NW, Washington, DC 20420.

Henry, James A., et al., "Computer-Automated Tinnitus Assessment Using Patient Control of Stimulus Parameters," Journal of Rehabilitation Research and Development, Nov./Dec. 2004, pp. 871-888, vol. 41, No. 6A, U.S. Department of Veterans Affairs, 810 Vermont Avenue, NW, Washington, DC 20420.

* cited by examiner

Edit Test Properties -- Hearing Threshold

Editable

- ☑ Stimulus Ear — left
- ☑ Number of Responses — 2
- ☑ Test-Retest Tolerance (dB) — 10
- ☑ Tolerance-Exceed Retries — 2
- ☑ Frequency Range Minimum (Hz) — 1000
- ☑ Frequency Range Maximum (Hz) — 4000
- ☑ Frequency Step (Octave) — 1
- ☑ Pulsed Tone — On
- ☑ No Response End Test — Yes -two retries
- ☑ Timeout at Min/Max (secs) — 3
- ☑ Response Time Window (secs) — 30

Save Changes

FIG. 4A

| Edit Test Properties -- Loudness Match | |
|---|---|
| *Editable* | |
| ☑ Number of Responses | 2 ▼ |
| ☑ Test-Retest Tolerance (dB) | 10 ▼ |
| ☑ Pulsed Tone | On ▼ |
| ☑ No Response End Test | Yes -two retries ▼ |
| ☑ Timeout at Min/Max (secs) | 3 ▼ |
| ☑ Response Time Window (secs) | 30 ▼ |
| | Save Changes |

FIG. 4B

| Edit Test Properties -- Pitch Match | |
|---|---|
| *Editable* | |
| ☑ Number of Responses | 2 ▼ |
| ☑ Pulsed Tone | On ▼ |
| ☑ Response Time Window (secs) | 30 ▼ |
| ☑ Pitch Match Check | Yes ▼ |
| | Save Changes |

FIG. 4C

| Edit Test Properties -- Bandwidth Match | |
|---|---|
| Editable | |
| ☑ Start Band | Random |
| ☑ Response Time Window (secs) | 30 |
| ☑ Coarse Matching | On |
| ☑ Fine Matching | On |
| | Save Changes |

FIG. 4D

| Edit Test Properties – Minimum Masking Level | |
|---|---|
| Editable | |
| ☑ Ear(s) To Be Tested | both |
| ☑ Stimulus Type | 2-12 kHz Noise |
| ☑ Max Output (dB) | 100 |
| ☑ Starting Intensity – Threshold (dB) | 20 |
| ☑ Starting Intensity Delta – Masking | -5 |
| ☑ Number of Responses – Threshold | 2 |
| ☑ Number of Responses – Masking | 2 |
| ☑ Response Time Window (secs) | 30 |
| ☑ Timeout at Min/Max (secs) | 3 |
| ☑ No Response – End Test | Yes – two retries |
| ☑ Test-Retest Tolerance (dB) | 10 |
| ☑ Tolerance-Exceed Retries | 2 |

Save Changes

FIG. 4E

Edit Test Properties -- Residual Inhibition

Editable

☑ Length of Stimulus (secs)   30
☑ Initial Data (dB)   10
☑ Patient Control (dB)   5
☑ Response Duration (minutes)   0:45

Save Changes

FIG. 4F

| Sound # | Bandwidth Variable/Fixed | Bandwidth | Sounds for "Coarse" Matching Mode |
|---|---|---|---|
| 0 | Fixed | Pure tone at PMF | Pure tone |
| 1 | Fixed | 1.7 Hz | Narrowband noise |
| 2 | Fixed | 3 Hz | |
| 3 | Fixed | 5 Hz | |
| 4 | Fixed | 10 Hz | |
| 5 | Fixed | 15 Hz | |
| 6 | Fixed | 30 Hz | |
| 7 | Fixed | 50 Hz | |
| 8 | Fixed | 90 Hz | |
| 9 | Fixed | 150 Hz | |
| 10 | Fixed | 270 Hz | |
| 11 | Variable | PMF/Q (Q=50) | Wideband noise |
| 12 | Variable | PMF/Q (Q=20) | |
| 13 | Variable | PMF/Q (Q=10) | |
| 14 | Variable | PMF/Q (Q=5) | |
| 15 | Variable | PMF/Q (Q=1) | |

Sounds 0–10 grouped as 40; sounds 11–15 grouped as 42.

FIG. 5

METHOD AND APPARATUS FOR TINNITUS EVALUATION

CROSS REFERENCE TO RELATED APPLICATIONS

The present application is a continuation of U.S. patent application Ser. No. 12/374,274, filed Sep. 22, 2009, which is a U.S. National Phase patent application of PCT/US2007/073663, filed Jul. 17, 2007, which is a non-provisional application of, and claims priority to, provisional application 60/807,696, filed on Jul. 18, 2006. The specification of the provisional application is hereby incorporated in its entirety, except for those sections, if any, that are inconsistent with this specification.

STATEMENT REGARDING FEDERALLY SPONSORED RESEARCH OR DEVELOPMENT

The present invention was made with United States government support awarded by the following agency: Veterans Affairs (VA) Rehabilitation, Research & Development (RR&D) Service, under the following contract/grant number: 02-1103 (Review Group C3210R). The United States may have certain rights in this invention.

TECHNICAL FIELD

Embodiments of the invention relate generally to the field of hearing and hearing assessment, specifically to methods, apparatuses, and systems associated with tinnitus evaluation.

BACKGROUND

Tinnitus is a psychoacoustic phenomenon experienced by many people, at least as a transient event. Tinnitus is signified by a perception of sounds usually having no source outside of the tinnitus patient's auditory nervous system. For some forms of tinnitus, the source of the sounds (somatosounds) is somewhere in the body, usually in the head and/or the neck region. In any event, although some tinnitus patients are able to adapt to the condition without the need for clinical intervention, others may experience severe distress including cognitive, emotional, and sleep disorders, any of which may impact everyday activities.

Although treatment options may be available to tinnitus patients, effective treatment of the condition depends at least in part on accurate clinical assessment. For example, it may be necessary to understand and quantify the particular sound(s) of the patient's tinnitus manifestation (e.g., spectral location and/or loudness). In addition, it may be desirable to monitor changes, if any, in a patient's tinnitus to measure efficacy of a prescribed course of treatment.

Currently, various tests may be used to assess tinnitus. For example, pitch and loudness matching may be performed and generally involve matching between a patient's tinnitus and a pure tone. However, in some cases, a patient's tinnitus may manifest itself more as a range of tones than as a single tone. Various other techniques may include masking levels to determine the level (loudness) of sound that just barely masks (covers) the sound of a patient's tinnitus. Still further, testing for residual inhibition may be performed to determine whether any reduction in loudness of a patient's tinnitus occurs as a result of acoustic stimulation.

Despite the various tests that may be used for assessing a patient's tinnitus, standard test protocols for clinical assessment of tinnitus are virtually non-existent. Thus, repeating any given testing protocol for the same and/or different patients may be impossible, particularly if more than one clinician administers diagnostic assessments. Furthermore, determining a meaningful comparison between the severities of patients' tinnitus may be impossible due to this introduction of variables to the testing protocol.

BRIEF DESCRIPTION OF THE DRAWINGS

Embodiments of the present invention will be readily understood by the following detailed description in conjunction with the accompanying drawings. Embodiments of the invention are illustrated by way of example and not by way of limitation in the figures of the accompanying drawings.

FIG. 4A-FIG. 4F are templates for tinnitus evaluation tests incorporated with the teachings of the present invention, in accordance with various embodiments;

FIG. 5 illustrates a tinnitus evaluation method incorporated with the teachings of the present invention, in accordance with various embodiments.

DETAILED DESCRIPTION OF EMBODIMENTS OF THE INVENTION

Figure 1:
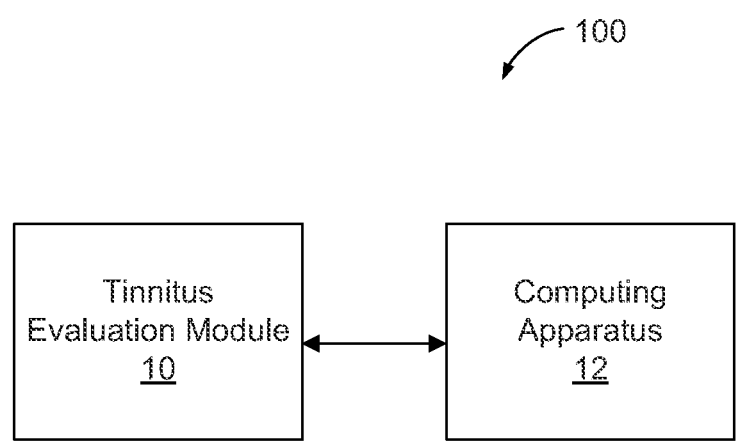
FIG. 1 illustrates a tinnitus evaluation system incorporated with the teachings of the present invention, in accordance with various embodiments.

In the following detailed description, reference is made to the accompanying drawings which form a part hereof and in which is shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

Various operations may be described as multiple discrete operations in turn, in a manner that may be helpful in understanding embodiments of the present invention; however, the order of description should not be construed to imply that these operations are order dependent.

The description may use the phrases "in an embodiment," "in embodiments," or "in various embodiments," which may each refer to one or more of the same or different embodiments. Furthermore, the terms "comprising," "including," "having," and the like, as used with respect to embodiments of the present invention, are synonymous.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" means A or B. For the purposes of the description, a phrase in the form "A and/or B" means "(A), (B), or (A and B)". For the purposes of the description, a phrase in the form "at least one of A, B, and C" means "(A), (B), (C), (A and B), (A and C), (B and C), or (A, B and C)". For the purposes of the description, a phrase in the form "(A)B" means "(B) or (AB)" that is, A is an optional element.

Embodiments of the present invention are directed to methods, articles of manufacture, and systems for evaluating tinnitus. In exemplary embodiments, a computing system may be endowed with one or more components of the disclosed articles of manufacture and/or systems and may be employed to perform one or more methods as disclosed herein. In various embodiments, tinnitus may be evaluated using one or more of various tinnitus testing protocols, which may include those as described herein. Testing protocols as described may be used to assess tinnitus through one or more automated tests measuring parameters of tinnitus manifestation resulting in a standardized testing protocol to accurately, reliably, and rapidly measure tinnitus in a repeatable manner.

It should be noted that although the following discussion generally refers to a user in terms that generally equate with a patient or a person being tested for tinnitus, various embodiments of the present invention may also be used by a person implementing testing such as, for example, a clinician.

Referring now to FIG. 1, illustrated is a tinnitus evaluation system 100 in accordance with various embodiments of the present invention. As illustrated, system 100 may comprise a tinnitus evaluation module 10 operatively coupled to a computing apparatus 12. Tinnitus evaluation module 10 may be configured to generate one or more sounds according to a tinnitus evaluation protocol as may be instructed by a computing apparatus 12.

In various embodiments, computing apparatus 12 may be configured to cause sounds to be generated by tinnitus evaluation module 10, in accordance with a test for evaluating and/or treating tinnitus. For example, computing apparatus 12 may be configured to cause sounds to be generated in accordance with a test selected from the group consisting of a hearing threshold test, a loudness match test, a pitch match test, a bandwidth match test, a minimum masking level test, and a residual inhibition test, as described more fully herein.

Computing apparatus 12 may comprise any computing apparatus suitable for the purpose. For example, according to various embodiments, a personal computer may be suitable. A portable personal computer (e.g., a notebook/laptop computer) may provide desirable size and/or portability characteristics, depending on the applications. Other computing apparatuses may be similarly suitable.

Figure 2:
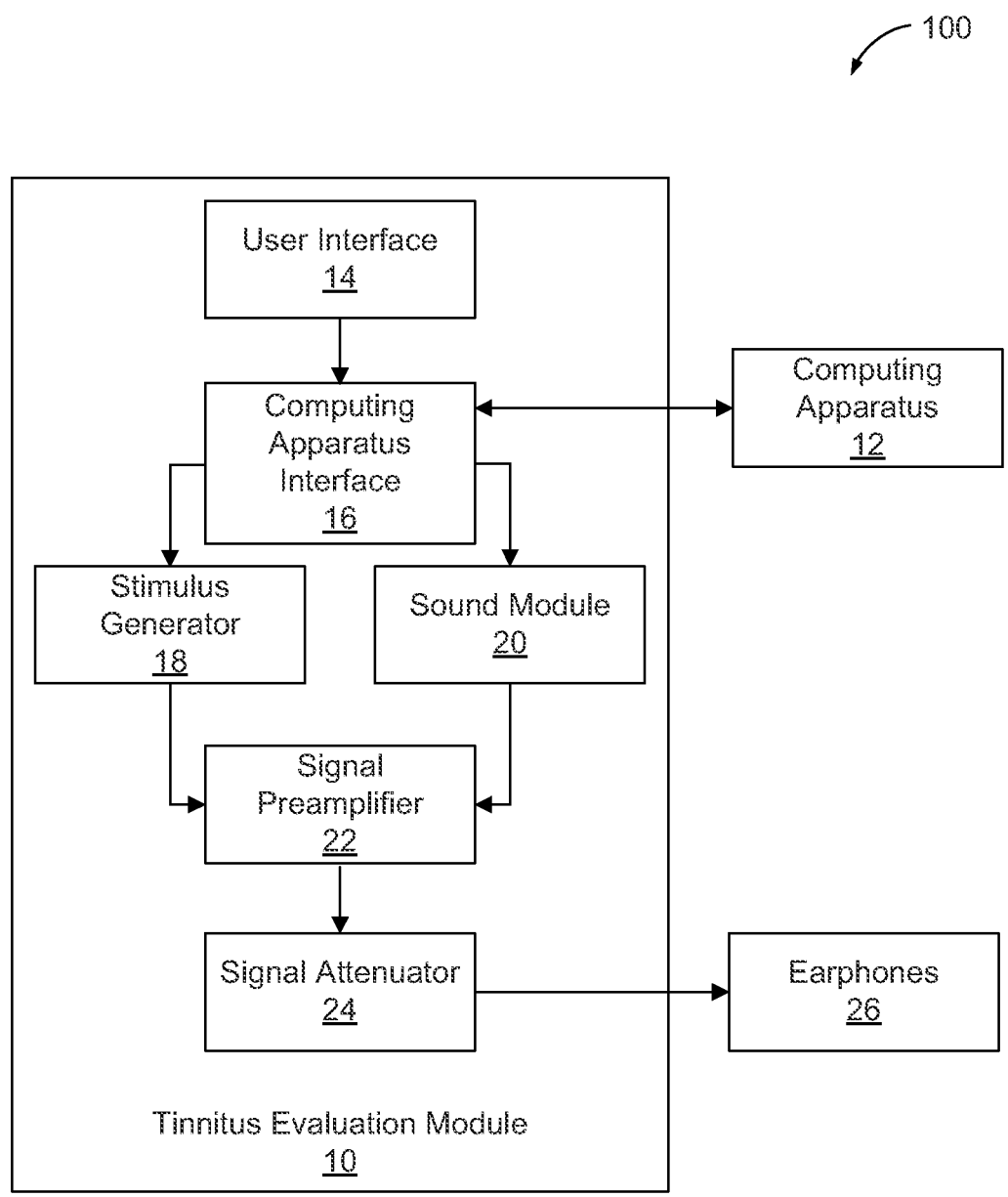
FIG. 2 illustrates another embodiment of the tinnitus evaluation system of FIG. 1 incorporated with the teachings of the present invention, in accordance with various embodiments.

Computing apparatus 12 and tinnitus evaluation module 10 of system 100 may be variously coupled. As illustrated in FIG. 2, for example, tinnitus evaluation module 10 and computing apparatus 12 may be operatively coupled by way of a computing apparatus interface 16. Although tinnitus evaluation module 10 and computing apparatus 12 may be permanently coupled, they may instead be configured to be reversibly coupled. Reversibly coupling tinnitus evaluation module 10 and computing apparatus 12 may advantageously allow for selectively coupling tinnitus evaluation module 10 to various computing apparatuses. In some embodiments, tinnitus evaluation module 10 may be smaller than computing apparatus 12 and so the capability to de-couple tinnitus evaluation module 10 from computing apparatus 12 may allow for portability of tinnitus evaluation module 10 that may otherwise be difficult.

To facilitate coupling tinnitus evaluation module 10 with computing apparatus 12, computing apparatus interface 16 may comprise a Universal Serial Bus (USB) to Serial Port bridge device. In various ones of these embodiments, the USB may also provide power to tinnitus evaluation module 10 from a power source integral to and/or coupled to system 100. In various other embodiments, computing apparatus 12 and tinnitus evaluation module 10 may be coupled, for example, by a wireless connection (e.g., a radio frequency connection, etc.), FireWire, or Recommended Standard (RS)-232. Those skilled in the art will recognize that other apparatuses and methods may be enlisted for operatively coupling computing apparatus 12 and tinnitus evaluation module 10 within the scope of the present invention.

To facilitate testing of one or both ears of a user (e.g., a patient or other subject), tinnitus evaluation module 10 may comprise a selected one or more of a stimulus generator 18, sound module 20, a signal preamplifier 22, and a signal attenuator 24 as illustrated in FIG. 2.

Stimulus generator 18 may be adapted to generate, or cause to be generated, one or more sounds. For example, stimulus generator 18 may be adapted to generate/cause to be generated one or more pure tones, octave band pass noises, and/or fixed width narrow band noises. Tinnitus evaluation module 10 may comprise a plurality of stimulus generators 18, and in various ones of these embodiments, stimulus generators 18 may each be controlled and used independently.

Stimulus generator 18 may be configured to generate/cause to be generated one or more sounds, any of which may be swept across a frequency range in a stepped or quasi-continuous manner. In an embodiment, numerical control of a center frequency and bandwidth may be possible with a resolution sufficient to allow sweeping of frequencies that is perceived by a user as continuous which may further allow for fine adjustment of a frequency and/or bandwidth with little or no delay or interruption in the presentation stimulus.

One or more stimulus generators 18 may each be configured to generate a certain type and/or range of stimuli. For example, stimulus generator 18 may be configured as a block of functional modules that are inter-connected using analog switches. In various embodiments, functional modules may comprise a programmable oscillator, a programmable state variable filter, a programmable noise source, and an analog multiplier. In various ones of these embodiments, the oscillator and state variable filter may be programmed with 12-bit digital-to-analog converters configured for use as numerically controlled potentiometers. The noise source may be implemented with an independent microcontroller which may execute various algorithms to produce low-pass filtered noise of various bandwidths. Still further, in various embodiments, stimulus generator 18 may be configured to operate in one or more modes. For example, stimulus generator 18 may be configured to operate in a selected one or more of pure tone mode, octave band-pass noise mode, and fixed width narrow-band noise mode.

In some embodiments, stimulus generator 18, or another feature of system 100 in accordance with various embodiments, may be adapted to generate/cause to be generated custom sounds. For example, a custom sound may be stored in system as a waveform audio format (WAV) file, or other file format, that may be played at a later time. A custom sound may be particularly useful for minimum masking level and/or residual inhibition testing wherein a band of noise may be used as part of a tinnitus evaluation test.

In various embodiments, tinnitus evaluation module 10 may comprise two independent signal preamplifiers 22, one for each channel of earphones 26 (right and left). Signal preamplifiers 22 may be variously configured. For example, signal preamplifiers 22 may be configured to perform a selected one or more of selecting an audio source for a particular earphone channel, leveling the audio source, and selectively muting the audio source for presentation of the stimuli. With respect to source selection, in various ones of these embodiments, signal preamplifiers 22 may be adapted to be digitally controlled to select an audio source via an 8-input analog signal multiplexer. With respect to leveling and muting the audio source, tinnitus evaluation module 10 may comprise a plurality of precision voltage controlled amplifiers for each earphone channel (right and left). In various embodiments, signal preamplifiers 22 may comprise a 10-bit digital-to-analog converter.

In various embodiments, tinnitus evaluation module 10 may comprise electronic volume-unit (VU) meters, and in various ones of these embodiments, tinnitus evaluation module 10 may use signal preamplifiers 22 in conjunction with the VU meters to adjust the amount of signal gain to ensure a consistent audio source level. In some embodiments, signal preamplifiers 22 may be adapted to suppress audio sources by some volume unit. For example, signal preamplifiers 22 may be adapted to suppress audio sources by 90 dB as a mute function. In embodiments, a mute function may control the presentation of stimuli, in either a continuous or pulsed fashion.

In various embodiments, audio signals selected and/or conditioned by signal preamplifiers 22 may be selectively attenuated by signal attenuator 24. Tinnitus evaluation module 10 may comprise one or more signal attenuators 24. In various embodiments, for example, tinnitus evaluation module 10 may comprise two signal attenuators 24, one for each channel of earphones 26 (right and left).

Signal attenuators 24 may be numerically controlled and may be configured to span a predetermined frequency range in predetermined frequency increments. In embodiments, for example, signal attenuators 24 may have a range of over 120 dB and may progress in 0.5 dB steps. Signal attenuators 24 may comprise zero-cross detection circuits to permit changing signal attenuation settings without the need to mute the stimulus.

Attenuated signals may be buffered by low noise, bridged output power amplifiers in order to produce the desired stimuli in earphones 26. In various ones of these embodiments, power amplifiers may be adapted to provide current and voltage sufficient to drive earphones 26 with a predetermined impedance. For example, in some embodiments, power amplifiers may be adapted to provide current and voltage sufficient to drive earphones 26 with an impedance of 32 to 150 Ohms. Further, in various embodiments, a resistive output pad may be selectively inserted into the signal path between the power amplifier and an earphone transducer which may provide an additional 20 dB of "post" attenuation. An output pad may have the effect of reducing background noise which may enable earphones 26 to produce higher quality stimuli at low to moderate output levels. An output pad may be removed if desired when high output levels are necessary.

Tinnitus evaluation module 10 may include a sound module 20. For various embodiments, sound module 20 may be adapted to enable tinnitus evaluation module 10 to play back recorded speech, verbal instructions, and/or demonstration audio. In various ones of these embodiments, tinnitus evaluation module 10 may comprise a USB-enabled digital-to-analog converter for playing the audio. The converter may allow tinnitus evaluation module 10 to be recognized by one or more other components of tinnitus evaluation system 100 as a standard multimedia device, allowing tinnitus evaluation module 10 to function like a sound card. In various embodiments, digitally recorded audio materials played through tinnitus evaluation module 10 including the converter are electronically routed through a normal audio signal path in tinnitus evaluation module 10 for precise control of the presentation and audio level.

Tinnitus evaluation module 10 may be configured to be controlled by a user by way of user interface 14. User interface 14 may be any interface suitable for the purpose, including, for example, one or more switches, one or more knobs, and/or a touchscreen, etc. A switch and/or a knob may be a general-purpose device whose functionality may be assigned as desired, depending on the applications. A suitable knob may be an optical encoder type having no stops in either direction and may be completely silent in operation. A knob may be optionally set to control a number of different internal functions in tinnitus evaluation module 10, including sound levels, tone frequency, and/or noise bandwidths. In various embodiments, a knob may allow a patient to control a selected one or more of a pitch, band, and loudness of a sound during one or more tinnitus evaluation tests.

Although not illustrated, various exemplary embodiments of tinnitus evaluation module 10 may comprise a non-volatile memory device for storing data as needed. For example, the memory device may store calibration information, service information, device options, history, and/or other information.

Figure 3:
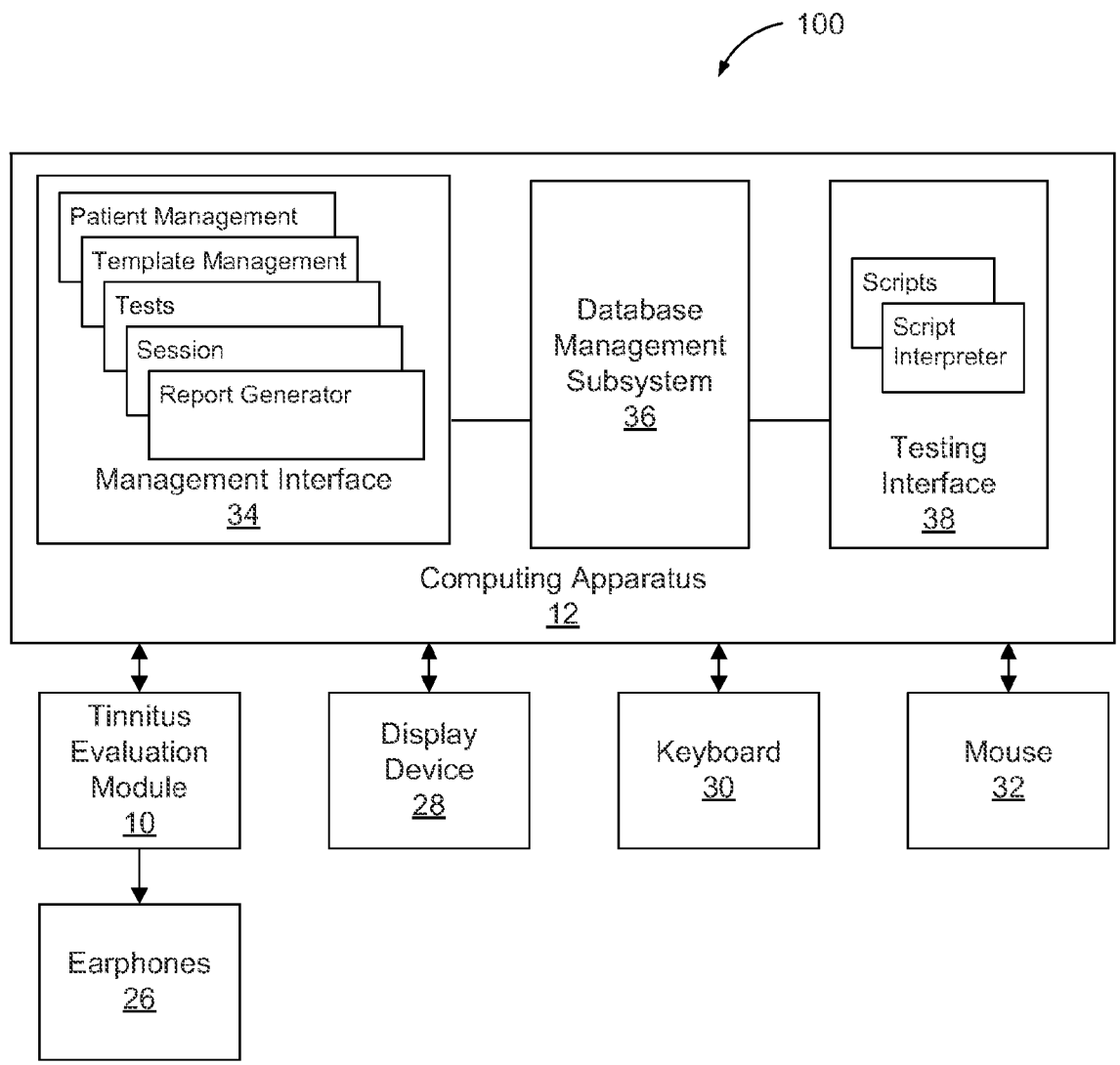
FIG. 3 illustrates another embodiment of the tinnitus evaluation system of FIG. 1 incorporated with the teachings of the present invention, in accordance with various embodiments.

Turning now to FIG. 3, illustrated is another exemplary embodiment of tinnitus evaluation system 100. As illustrated, tinnitus evaluation system 100 includes tinnitus evaluation module 10 and computing apparatus 12. To facilitate testing of one or both of a user's ears, tinnitus evaluation system 100 may include earphones 26 to present sound(s) directly to the user's ear(s). Tinnitus evaluation system 100 may include one or more of various input/output devices including, for example, a display device 28, a keyboard 30, and a mouse 32.

Computing apparatus 20 may include a management interface 34, a database management subsystem 36, and a testing interface 38 for implementing various tasks.

In various embodiments, management interface 34 may allow a user to manage tinnitus evaluation system 100. For example, management interface 34 may allow for one or more of the management of patients, management of test templates, running of tinnitus evaluation tests, generation of reports, and management testing sessions. Management interface 34 may be any application written in any programming language suitable for the purpose. For example, in some embodiments, management interface 34 may be a Microsoft Windows application written in C++.Net. According to various embodiments, management interface 34 may use .NET windows and control objects to render management interface screens. Windows may include one or more of a patient management window, a template management window, a test window, a session window, and a report generator window.

Testing interface 38 may comprise one or more scripts and one or more script interpreters. Testing interface 38 may be adapted to run one or more tinnitus evaluation tests via a script interpreter and one or more test scripts. In various embodiments, a script interpreter may be adapted to enable computing apparatus 12 and/or tinnitus evaluation module 10 to perform a tinnitus evaluation test according to instructions of one or more scripts. According to various embodiments, the script interpreter may provide one or more instructions to tinnitus evaluation module 10 to cause tinnitus evaluation module 10 to generate one or more sounds for a tinnitus evaluation test.

Testing interface 38 may be configured to enable computing apparatus 12 to be calibrated as needed by way of a calibration subsystem. In various ones of these embodiments, a calibration subsystem may comprise a script in testing interface 38, wherein the script enables computing apparatus 12 to calibrate system 100 by using the same scripting language an interpreter used or would use for session testing. In various embodiments, calibration data may be stored in tinnitus evaluation module 10 and/or some other part of system 100.

Database management subsystem 36 may be adapted to store test configurations and patient information for running the tests. In various embodiments, system 100 may be adapted to record test results to database management subsystem 36, and system 100 may also be adapted to later retrieve and/or receive the test results to generate report(s) of the test results. In various embodiments, database management subsystem 36 may be adapted to manage and/or control communication and/or interaction between management interface 34 and testing interface 38.

System 100 may be configured to store various information as needed. For instance, system 100 may be adapted to store parameters and/or configurations of the tinnitus evaluation tests. Parameters may include which ear(s) of the user are to be tested, frequency ranges, length of sound stimuli, etc. In various embodiments, default configurations and/or sequences of testing may be stored by system 100. Some parameters and configurations may be configured to be editable while others are un-editable. For example, if tinnitus evaluation tests are interdependent, the sequence of those tests may be important and may be configured so that the sequence is un-editable.

System 100 may be adapted to store one or more of user information, test results, patient information, session information, and response information. Additionally or alternatively, various other information may be stored, depending on the application. In some embodiments, user information may include login information for users who administer testing. In some embodiments, session information may include information about each user's testing event such as duration, completion, and any parameter(s) that may have been edited from the default settings. Response information may include data generated during a testing session.

In various embodiments, system 100 may be adapted to allow a user to perform various tasks. For example, system 100 may be adapted to allow a user to configure and/or launch various tinnitus evaluation tests. In some embodiments, system 100 may be adapted to generate, or cause to be generated, reports of various information including, for example, reports of the results of tinnitus tests run for one or more user. Still further, in various embodiments, system 100 may be adapted to allow a user to manage patient information. Information for a new patient may be input and/or information for existing patients may be edited. For example, in some of these embodiments, a user may input/edit a patient's name, age, tinnitus characteristics, etc.

In embodiments, system 100 may be adapted to cause sounds to be generated in accordance with a test for evaluating and/or treating tinnitus when a test is launched. In an embodiment, once initiated, a test may run from start to finish without the need for input or manipulation by a clinician, but rather may be guided by the responses of the patient. In various ones of these embodiments, once a test is launched, system 100 may be adapted to automatically cause sounds to be generated in accordance with the test, and in some cases, may be dependent upon a patient's prior response(s). In various embodiments, system 100 may be adapted to cause sounds to be generated one at a time with each sound only in response to some action by a user.

System 100 may display on display device 28 instructions and/or information for a user. In embodiments, display device 28 may be adapted to receive an input (e.g., by a touch screen, actuation of an icon, manipulation of an input device such as a joystick or knob, etc.) and the input may, in some cases, be communicated (actively and/or passively) to computing system 12. In exemplary embodiments, display device 28 may provide information and/or instructions to a user in accordance with a tinnitus evaluation test, and computing system 12 may cause sounds to be generated in accordance with the test to which a user may respond. For example, if a test requires a patient's response (e.g., during a loudness test, a patient may need to identify a loudness of a tone matching a loudness of the patient's tinnitus), an instruction in accordance with the required response may be provided to the patient and/or a clinician in accordance therewith.

In various embodiments, system 100 may be adapted to generate an alert. For example, system 100 may be adapted to call, page, email, and/or otherwise alert a clinician or some other person as needed. System 100 may comprise an interface wherein a user may submit a request for an alert and, in some cases, system 100 may be adapted to generate the alert in response thereto. In embodiments, an interface may comprise one or more of an icon on display device 28, a button, a switch, etc., any of which may be adapted to cause an alert to be generated.

As discussed herein, system 100 may be adapted to cause tinnitus evaluation module 10 to generate sounds in accordance with a tinnitus evaluation test. A tinnitus evaluation test may be enlisted for assessing and/or quantifying tinnitus. In various embodiments, the tests may include one or more of the following tests: hearing threshold, loudness match, pitch match, bandwidth match, minimum masking level, and residual inhibition. Those skilled in the art will recognize that other tests similarly may be implemented using various embodiments of the present invention.

Various parameters for the tinnitus evaluation tests may be pre-set using management interface 34 as described herein with reference to FIG. 3. Exemplary templates for various tinnitus evaluation tests including parameters of the tests are illustrated in FIG. 4A-FIG. 4F. It should be noted that the templates are set forth herein for exemplary purposes only and should not be construed as limiting which parameters are included in a test or the values thereof.

With regard to a hearing threshold test (see, e.g., FIG. 4A), such a test may be conducted to determine a patient's minimum audibility of a tone. In various embodiments, a tone at a frequency may be presented to the patient and a loudness of the tone that is just barely audible to the patient may be identified. The hearing threshold test may be repeated as desired, and in such embodiments, the results thereof may be averaged or otherwise calculated to determine a final hearing threshold. The hearing threshold test may be performed at one or more frequencies, depending on the application, and in various ones of these embodiments, the hearing threshold test may be performed for a series of frequencies.

A loudness match test (see, e.g., FIG. 4B) may be performed to determine a loudness of a frequency matching a patient's tinnitus loudness. In various ones of these embodiments, the loudness match test may follow a hearing threshold test and may be based at least in part on result(s) of the hearing threshold test. In embodiments, the loudness match test may be performed by generating a tone and identifying a loudness of the tone matching a loudness of the patient's tinnitus. The loudness match test may include loudness match testing at each frequency at which a hearing threshold was conducted, either after each frequency is tested for hearing threshold or after a series of frequencies has been tested for hearing threshold (i.e., the testing may proceed as: hearing threshold at frequency A—loudness match at frequency A—hearing threshold at frequency B—loudness match at frequency B—etc.; or, alternatively, the testing may proceed as: hearing threshold at frequency A—hearing threshold at frequency B—loudness match at frequency A—loudness match at frequency B—etc.). In various embodiments, a loudness match test may be repeated one or more times, as desired, and in various ones of these embodiments, result(s) of multiple loudness match tests may be averaged or may have other calculations performed thereto to determine a final loudness match.

A pitch match test (see, e.g., FIG. 4C) may be performed to determine one or more frequencies matching a patient's tinnitus pitch. The pitch match test may be based at least in part on result(s) of a hearing threshold and/or loudness match test. For example, in various embodiments, the pitch match test may be performed by presenting the patient with one or more sounds, each sound having a pitch and/or loudness selected by the patient during a hearing threshold and/or loudness match test. The pitch match test may be repeated one or more times, as necessary or desired, and in various ones of these embodiments, result(s) of multiple pitch match tests may be averaged or otherwise calculated to determine a final pitch match.

In various embodiments, hearing threshold, loudness match, and pitch match testing may be conducted using pure tones, i.e., single-frequency sounds. A patient's tinnitus may not necessarily manifest itself in pure tones, however. Instead, the patient's tinnitus may be more noise-like (i.e., two or more different tones in combination). Accordingly, it may be desirable to test the patient's tinnitus manifestation using a combination of two or more tones to determine the sound of the patient's tinnitus more accurately. To this end, a bandwidth match test may be conducted to determine whether the patient's tinnitus manifests itself as a more tonal sound or as a more noise-like sound.

A bandwidth match test (see, e.g., FIG. 4D) may be conducted by presenting a patient with a predetermined pitch-match frequency and one or more noise-like sounds centered around the predetermined pitch-match frequency, and identifying which of the sounds more closely resembles the sound of the patient's tinnitus. In various embodiments, a bandwidth match test may comprise a "coarse" bandwidth matching and/or a "fine" bandwidth matching to obtain a more accurate match to the patient's tinnitus sound. One or more aspects of a bandwidth match test may be repeated one or more times, as desired, and in various ones of these embodiments, results may be averaged or may have other calculations performed thereto, as necessary or desired.

In various embodiments, a minimum masking level (MML) test (see, e.g., FIG. 4E) may be performed to determine a loudness of noise that just barely masks the loudness of a patient's tinnitus. In embodiments, a noise may be presented to the patient's ears, one at a time, and a loudness of the noise that is just audible to the patient may be identified. The patient may be presented with the noise binaurally (in some cases monaurally) and then a loudness covering the tinnitus in both of the patient's ears may be identified. The MML test may be repeated one or more times, and in various ones of these embodiments, results may be averaged or may have other calculations performed thereto to determine a final MML.

In various embodiments, a patient may be tested for residual inhibition (see, e.g., FIG. 4F). Residual inhibition generally refers to the phenomenon of a reduction in loudness of a patient's tinnitus as a result of stimulation (e.g., wide-band noise). According to various embodiments, the patient may be presented with a noise and any effect on the patient's tinnitus may be identified. In various embodiments, the patient may be presented with a noise based at least in part on an MML value determined for the patient. For example, the patient may be presented with a noise having a loudness greater than the patient's MML value and any effect on the patient's tinnitus may be identified. In embodiments, a noise may be presented to the patient for any one of various time periods, as desired. The residual inhibition test may comprise multiple presentations of a noise, with each noise separated by a pause. Still further, in various embodiments, the residual inhibition test may be repeated as necessary or desired.

Exemplary Testing Protocol

For exemplary purposes, embodiments of a testing protocol will now be presented. In these embodiments, a hearing threshold test, a loudness match test, a pitch match test, a bandwidth match test, an MML test, and a residual inhibition test may be performed.

In the following discussion, a tinnitus evaluation test may require a patient to respond to sounds presented to the patient. Although a response may be effected by any method suitable for the purpose, for various embodiments display device 28 of system 100 may display to the patient a prompt requesting some action. The patient may indicate a response or may otherwise respond to the prompt by way of user interface 14. So, for example, if the patient is prompted to adjust the loudness of a sound, the patient may do so by way of user interface 14.

The hearing threshold test may be performed by presenting a patient with a tone, for example a 1,000-Hz tone. The loudness at which the tone is just audible to the patient is identified. The patient may be presented with the sound another one or more times, and in various embodiments, the results may be averaged to determine a final hearing threshold for the tested frequency. Depending on the application, the hearing threshold test may be repeated for another frequency. For example, in various embodiments, the hearing threshold test may be performed for a series of frequencies (e.g., 1,000 Hz through 16,000 Hz, in ⅓-octave steps).

The hearing threshold test may be followed by a loudness match test to determine loudness of a tone matching the patient's tinnitus loudness. The loudness match test may be implemented by generating a tone at a frequency at which a hearing threshold test was conducted (e.g., 1,000 Hz) and prompting the patient to reduce/increase the volume of the tone to a point at which the tone matches a loudness of the patient's tinnitus. Similarly to the hearing threshold test, the loudness match test may be repeated one or more times for each frequency, and in various ones of these embodiments, the results averaged to determine a final loudness match for each frequency. In embodiments, the loudness match test may include loudness match testing at each frequency at which the hearing threshold is conducted.

The pitch match test may follow the hearing threshold test/loudness match test sequence. As noted above, hearing threshold and loudness match tests may determine loudness for each of one or more frequencies matching the patient's tinnitus loudness. Put another way, if three frequencies are tested for the patient using the hearing threshold and loudness matching tests, then three frequency/loudness tones (i.e., "pitches") have been determined for the patient. The pitch match test may then be conducted to determine which of the pitches most closely matches the pitch of the patient's tinnitus.

A bandwidth test may also be performed. In various embodiments, the bandwidth test may be performed by presenting the patient with a predetermined pitch-match frequency (e.g., as determined in the previously-discussed hearing threshold, pitch match, and loudness tests) and one or more noise-like sounds centered around the predetermined pitch-match frequency, with the patient prompted to indicate which of the sounds most closely resembles the sound of the patient's tinnitus. In various embodiments, the bandwidth test may proceed by first conducting a "coarse" bandwidth matching and then conducting a "fine" bandwidth matching to obtain a more accurate match to the patient's tinnitus sound. The coarse bandwidth testing may be conducted by presenting the patient with a pitch-match sound, narrow-band noise, and wide-band noise. The narrow-band noise may be narrowly centered around the pitch-match frequency; for example, the narrow-band noise may be a fixed 15-Hz-wide band of noise centered around the pitch-match frequency. The wide-band noise may be centered around the pitch-match frequency more widely than the narrow-band noise. The patient may then indicate which of the three sounds most closely resembles the patient's tinnitus. In various ones of these embodiments, the test may be repeated.

Fine bandwidth matching may follow coarse bandwidth matching. Sounds used for fine bandwidth matching may be dependent upon the sounds the patient selects during coarse bandwidth matching. More specifically, if during coarse bandwidth matching the patient selects a majority of sounds to pitch-match frequency and/or narrow-band noise, the patient may then be presented with a number of narrow-band sounds during fine bandwidth matching. Similarly, if during coarse bandwidth matching the patient selects a majority of sounds to wide-band noise, the patient may then be presented with a number of wide-band sounds during fine bandwidth matching.

During fine bandwidth matching, the patient may be presented with sounds on a finer scale than during coarse bandwidth matching in order to home in on the sound most closely resembling the patient's tinnitus. For example, in various embodiments and as shown in FIG. 5, if the patient selects more narrow-band sounds during coarse bandwidth matching, then the patient may be presented with sounds ranging from the pitch-match frequency through a 270-Hz-wide band of noise centered around the pitch-match frequency, as shown at 40. The patient may be given the option of sequencing through the sounds to select the sound most closely resembling the sound of the patient's tinnitus. In various embodiments, the fine bandwidth matching may be repeated any number of times and the results may then be averaged to determine a final bandwidth-match. On the other hand, in various embodiments, if the patient selects more wide-band sounds during coarse bandwidth matching, then the patient may be presented with sounds having wider bands of noise centered around the pitch-match frequency, the sounds increasing in bandwidth on intervals, as shown at 42, depending on the pitch-match frequency. The patient may be then presented with the final bandwidth-match sound and may rate the sound on how closely the sound matches the sound of the patient's tinnitus (e.g., "exact match," "very close," "somewhat close," "somewhat different," "not a match").

The MML test may be performed to determine the loudness of wide-band noise that just barely masks (makes inaudible) the patient's tinnitus. In various embodiments, the MML test may comprise presenting to each of the patient's ears, one at a time, a wide-band noise, and the patient then indicating a loudness of the noise that is just audible to the patient ("wide-band threshold noise"). The patient may then be presented, binaurally, a noise ("initial MML noise") at some level relative to the wide-band threshold noise selected by the patient. For example, the level may be 5 dB below the wide-band threshold. The initial MML noise in this example may be variously described as a −5 dB Sensation Level (−5 dB SL). Upon presenting the initial MML noise to the patient, the patient may then adjust the initial MML noise to a loudness that just covers the tinnitus in both of the patient's ears. In various embodiments, the MML test may be repeated and the results averaged to determine the final MML. MML testing can also be done in each ear separately (monaurally).

The patient may also be tested for residual inhibition. As mentioned herein, residual inhibition refers to the phenomenon of a reduction in loudness of the patient's tinnitus as a result of stimulation (e.g., wide-band noise). In various embodiments, the patient may be requested to listen to the loudness of their tinnitus, and then the patient may be presented, binaurally, with a noise 10 dB above the final MML value determined as discussed previously. In various ones of these embodiments, the noise may be presented to the patient for a 1-minute period, for example, and then discontinued. After discontinuing the noise, the patient may be instructed to indicate if their tinnitus loudness changed as a result of the noise. The patient may be requested to continually monitor the residual effect of the noise on their tinnitus for several minutes (e.g., 3 minutes), with a pause between each of the patient's responses (e.g., a 5 second pause between responses).

In various embodiments, a patient's response(s) to one or more of the previously discussed tinnitus tests may provide data from which a diagnosis of tinnitus, and/or some other correlation, may be determined. For example, in some embodiments, the patient's response(s) to one or more tinnitus tests may be analyzed and/or correlated to a predetermined standard in making a diagnosis of tinnitus. In various embodiments, the patient's response(s) to one or more tinnitus tests may form a dataset and/or may be output as a dataset from which a diagnosis may be made.

A tinnitus evaluation system (see, e.g., 100 of FIG. 1 and/or FIG. 3) may be adapted to output a selected one or more of a dataset, a diagnosis, and data of the patient's response(s) in relation to a standard (e.g., data for a person without tinnitus). In various ones of these embodiments, a diagnosis may be variously outputted. For example, the diagnosis may be simply a binary output such as a patient "has tinnitus" or "does not have tinnitus." However, in various other embodiments, the diagnosis may be a spectrum of diagnoses (e.g., "no tinnitus," "mild tinnitus," or "severe tinnitus"). In still other embodiments, data of the patient's response(s) may be output in a manner such that the patient's tinnitus manifestation can be graphically and/or numerically related to typical data for person(s) without tinnitus and/or having various degrees of tinnitus manifestation. The foregoing illustrative embodiment's diagnosis and/or correlation of patient data are intended for exemplary purposes only and thus embodiments of the present invention are not limited to the embodiments discussed.

Figure 6:
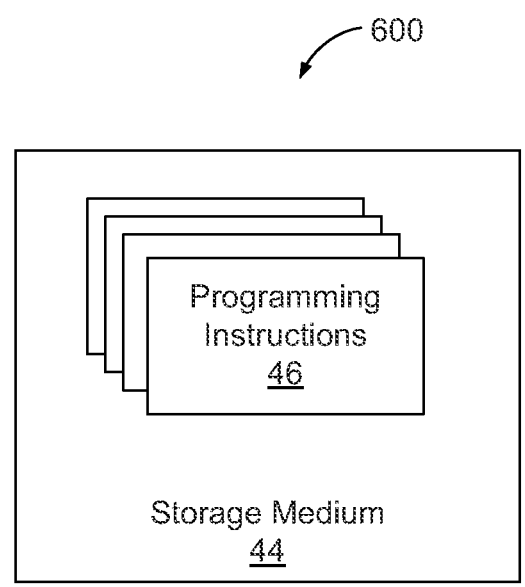
FIG. 6 illustrates an article of manufacture for evaluating tinnitus incorporated with the teachings of the present invention, in accordance with various embodiments.

Turning now to FIG. 6, illustrated is an article of manufacture 600 in accordance with various embodiments of the present invention. As illustrated, article of manufacture 600 may comprise a storage medium 44 and a plurality of programming instructions 46 stored in storage medium 44. In various ones of these embodiments, programming instructions 46 may be adapted to program an apparatus to enable the apparatus to perform one or more of the previously discussed tinnitus tests. For example, in various embodiments, programming instructions 46 may be adapted to program an apparatus to enable the apparatus to perform a bandwidth match test. In various ones of these embodiments, programming instructions 46 may enable the apparatus to cause a tinnitus evaluation module to output a first single-frequency sound based at least in part on a pitch of a patient's tinnitus and cause a tinnitus evaluation module to output a narrow-band sound centered at the frequency of the first single-frequency sound.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

What is claimed is:

1. An apparatus for evaluating tinnitus, comprising:
at least one stimulus generator configured to generate a single-frequency sound based at least in part on a pitch of a patient's tinnitus, the stimulus generator further configured to generate a narrow-band sound centered at the frequency of the single-frequency sound; and
a display device configured to display a prompt requesting an indication of which one of the single frequency sound and the narrow-band sound is more similar to a sound of the patient's tinnitus.

2. The apparatus of claim 1, wherein the stimulus generator is configured to generate octave band pass noises and fixed-width narrow-band noises.

3. The apparatus of claim 1, wherein the stimulus generator comprises one or more devices selected from a group consisting of a programmable oscillator, a programmable state variable filter, a programmable noise source, and an analog multiplier.

4. The apparatus of claim 1, further comprising a computing apparatus interface for coupling the apparatus to a computing apparatus.

5. The apparatus of claim 4, wherein the stimulus generator is configured to generate sounds based at least in part on instructions received from the computing apparatus.

6. The apparatus of claim 1, further comprising a user interface for allowing the patient to selectively control the sounds generated by the stimulus generator.

7. The apparatus of claim 1, further comprising a signal preamplifier configured to selectively modify sounds generated by the stimulus generator.

8. The apparatus of claim 7, further comprising at least one signal attenuator configured to attenuate the modified sounds.

9. The apparatus of claim 8, wherein the apparatus comprises two signal attenuators including a first signal attenuator configured to output attenuated sounds to a right earphone and further including a second signal attenuator configured to output attenuated sounds to a left earphone.

10. A system for evaluating tinnitus, comprising:
a tinnitus evaluation module adapted to generate one or more sounds; and
a computing apparatus coupled to the tinnitus evaluation module and configured to:
cause the tinnitus evaluation module to output a single-frequency sound based at least in part on a pitch of a patient's tinnitus;
cause the tinnitus evaluation module to output a narrow-band sound centered at the frequency of the single-frequency sound; and
cause the tinnitus evaluation module to display on a display device a prompt requesting an indication of which one of the single frequency sound and the narrow-band sound is more similar to a sound of the patient's tinnitus.

11. The system of claim 10, wherein the computing apparatus is further configured to cause the tinnitus evaluation module to output a wide-band sound, the wide-band sound comprising a bandwidth wider than the narrow-band sound and centered at the frequency of the single-frequency sound.

12. The system of claim 10, wherein the tinnitus evaluation module includes a selected one or more of a stimulus generator, a signal preamplifier, and a signal attenuator.

13. The system of claim 10, wherein the computing apparatus is configured to cause the tinnitus evaluation module to perform one or more tests selected from the group consisting of a hearing threshold test, a loudness match test, a pitch match test, a bandwidth match test, a minimum masking level test, and a residual inhibition test.

14. The system of claim 10, wherein the computing apparatus is configured to cause the tinnitus evaluation module to perform a bandwidth match test and at least one test selected from the group consisting of a hearing threshold test, a loudness match test, a pitch match test, a minimum masking level test, and a residual inhibition test.

15. The system of claim 10, wherein the computing apparatus is configured to cause the tinnitus evaluation module to perform a hearing threshold test, a loudness match test, a pitch match test, a bandwidth match test, a minimum masking level test, and a residual inhibition test.

16. The system of claim 10, wherein the computing apparatus comprises a testing interface configured to provide instructions to the tinnitus evaluation module, and wherein the tinnitus evaluation module is configured to output the sounds based at least in part on the instructions.

17. An article of manufacture to facilitate tinnitus evaluation, comprising:
a non-transitory storage medium; and
a plurality of programming instructions stored in the non-transitory storage medium adapted to program a computing apparatus to enable the computing apparatus to:
cause a tinnitus evaluation module to output a single-frequency sound based at least in part on a pitch of a patient's tinnitus;
cause the tinnitus evaluation module to output a narrow-band sound centered at the frequency of the fiFt- single-frequency sound; and
cause the tinnitus evaluation module to display on a display device a prompt requesting an indication of which one of the single frequency sound and the narrow-band sound is more similar to a sound of the patient's tinnitus.

18. The article of manufacture of claim 17, wherein the programming instructions are adapted to program the computing apparatus to enable the computing apparatus to cause the tinnitus evaluation module to output a wide-band sound, the wide-band sound comprising a bandwidth wider than the narrow-band sound and being centered at the frequency of the single-frequency sound.

19. The article of manufacture of claim 17, wherein the programming instructions are adapted to program the computing apparatus to enable the computing apparatus to cause the tinnitus evaluation module to perform one or more tests selected from the group consisting of a hearing threshold test, a loudness match test, a pitch match test, a bandwidth match test, a minimum masking level test, and a residual inhibition test.

20. The article of manufacture of claim 17, wherein the programming instructions are adapted to program the computing apparatus to enable the computing apparatus to cause the tinnitus evaluation module to perform a bandwidth match test and at least one test selected from the group consisting of a hearing threshold test, a loudness match test, a pitch match test, a minimum masking level test, and a residual inhibition test.

21. The article of manufacture of claim 17, wherein the programming instructions are adapted to program the computing apparatus to enable the computing apparatus to cause the tinnitus evaluation module to perform a hearing threshold test, a loudness match test, a pitch match test, a bandwidth match test, a minimum masking level test, and a residual inhibition test.

22. A method for evaluating tinnitus in a patient, comprising:
   generating by a tinnitus evaluation module a first single-frequency sound based at least in part on a pitch of the patient's tinnitus;
   generating by the tinnitus evaluation module a narrow-band sound centered at the frequency of the first single-frequency sound; and
   displaying on a display device a prompt requesting an indication of which one of the first single-frequency sound and the narrow-band sound is more similar to a sound of the patient's tinnitus.

23. The method of claim 22, further comprising generating by the tinnitus evaluation module a wide-band sound, the wide-band sound comprising a bandwidth wider than the narrow-band sound and being centered at the frequency of the first single-frequency sound.

24. The method of claim 23, further comprising displaying on the display device a prompt requesting an indication of which one of the first single-frequency sound, the narrow-band sound, and the wide-band sound is most similar to the sound of the patient's tinnitus.

25. The method of claim 22, further comprising:
   generating by the tinnitus evaluation module a second single-frequency sound; and
   displaying on the display device a prompt requesting an indication of the patient's minimum audibility for the second single-frequency sound.

26. The method of claim 25, further comprising identifying a loudness of the second single-frequency sound most similar to a loudness of the patient's tinnitus.

27. The method of claim 26, further comprising:
   generating by the tinnitus evaluation module a third single-frequency sound;
   identifying a loudness of the third single-frequency sound most similar to the loudness of the patient's tinnitus; and
   displaying on the display device a prompt requesting an indication of which one of the second single-frequency sound and the third single-frequency sound is more similar to the pitch and the loudness of the patient's tinnitus.

28. The method of claim 22, further comprising:
   generating by the tinnitus evaluation module a first multi-frequency sound; and
   displaying on the display device a prompt requesting an indication of a loudness of the multi-frequency sound that masks a loudness of the patient's tinnitus.

29. The method of claim 28, further comprising:
   generating by the tinnitus evaluation module a second multi-frequency sound having a loudness greater than the loudness of the first multi-frequency sound; and
   after generating the second-multi-frequency sound, displaying on the display device a prompt requesting an indication of a change in the loudness of the patient's tinnitus.

* * * * *